(12) United States Patent
Jha et al.

(10) Patent No.: US 11,525,808 B2
(45) Date of Patent: Dec. 13, 2022

(54) DETECTING AND QUANTIFYING LIQUID POOLS IN HYDROCARBON FLUID PIPELINES

(71) Applicant: Halliburton Energy Services, Inc., Houston, TX (US)

(72) Inventors: Pranab Narayan Jha, Houston, TX (US); Srinivasan Jagannathan, Houston, TX (US); Ratheen Chaturvedi, Mumbai (IN)

(73) Assignee: Halliburton Energy Services, Inc., Houston, TX (US)

(*) Notice: Subject to any disclaimer, the term of this patent is extended or adjusted under 35 U.S.C. 154(b) by 749 days.

(21) Appl. No.: 16/515,446

(22) Filed: Jul. 18, 2019

(65) Prior Publication Data
US 2020/0182831 A1 Jun. 11, 2020

Related U.S. Application Data

(60) Provisional application No. 62/775,473, filed on Dec. 5, 2018.

(51) Int. Cl.
*G01N 29/032* (2006.01)
*G01N 33/28* (2006.01)
*G01N 29/44* (2006.01)

(52) U.S. Cl.
CPC ....... *G01N 29/032* (2013.01); *G01N 29/4481* (2013.01); *G01N 33/2823* (2013.01)

(58) Field of Classification Search
CPC ............. G01N 29/032; G01N 29/4481; G01N 33/2823

(Continued)

(56) References Cited

U.S. PATENT DOCUMENTS 6,993,963 B1 2/2006 Gudmundsson
9,097,601 B2 8/2015 Stephens et al.
(Continued)

FOREIGN PATENT DOCUMENTS

CA 2987168 12/2016
CN 109780447 A 5/2019
(Continued)

OTHER PUBLICATIONS

Ghidaoui et al., "A Review of Water Hammer Theory and Practice", Applied Mechanics Reviews, 58(1), Jan. 2005, pp. 49-76.
(Continued)

*Primary Examiner* — John Fitzgerald
*Assistant Examiner* — Rodney T Frank
(74) *Attorney, Agent, or Firm* — Kilpatrick Townsend & Stockton LLP

(57) ABSTRACT

Pressure-inducing devices and pressure transducers can be used to detect and quantify liquid pools in hydrocarbon fluid pipelines. Pressure fluctuations can be detected by a pressure transducer, where the pressure fluctuations are the response of a pressure-inducing device outputting a pressure signal in a pipe carrying hydrocarbons. Variation in a pipe diameter caused by pooling or deposition can be estimated using an inverse model. The pooling or depositions can be classified by applying a machine-learning model to the pressure fluctuations. The variation in pipe diameter can be converted to an equivalent liquid volume for pooling locations. A pooling or deposition location and volume can be output and used for determining an action on the pipe to remove the pooling or deposition.

20 Claims, 14 Drawing Sheets

(58) Field of Classification Search
USPC .......................................................... 702/54
See application file for complete search history.

(56) References Cited

U.S. PATENT DOCUMENTS

| | | |
|---|---|---|
| 2006/0225507 A1 | 10/2006 | Paulson |
| 2012/0041694 A1 | 2/2012 | Stephens et al. |
| 2012/0227499 A1* | 9/2012 | Amir ..................... G01N 29/043 73/622 |
| 2017/0212024 A1* | 7/2017 | Hunt ....................... G01N 27/00 |
| 2018/0172546 A1 | 6/2018 | Calzavara et al. |
| 2018/0202612 A1 | 7/2018 | Simpson et al. |

FOREIGN PATENT DOCUMENTS

| | | |
|---|---|---|
| JP | 2014507007 | 3/2014 |
| WO | 2017008100 | 1/2017 |
| WO | 2017011850 | 1/2017 |
| WO | 2019135737 A1 | 7/2019 |

OTHER PUBLICATIONS

Adeleke et al., "Blockage Detection and Characterization in Natural Gas Pipelines by Transient Pressure-Wave Reflection Analysis", SPE Journal, Apr. 2013, pp. 355-365.
Hanmaiahgari et al., "Identification of Partial Blockages in Pipelines Using Genetic Algorithms", Sadhana, vol. 42, No. 9, Sep. 2017, pp. 1543-1556.
NL Application No. NL2023772 , Office Action, dated Jun. 7, 2021, 8 pages.
RU. Application No. RU2021110425 , Office Action, dated Jan. 31, 2022, 7 pages.
PCT Application No. PCT/US2019/042389 , "International Search Report and Written Opinion", dated Oct. 25, 2019, 10 pages.
EP Application No. EP19892919.2, "Extended European Search Report", dated May 24, 2022, 7 pages.

\* cited by examiner

DETECTING AND QUANTIFYING LIQUID POOLS IN HYDROCARBON FLUID PIPELINES

CROSS REFERENCE TO RELATED APPLICATION

This claims priority to U.S. Provisional Application Ser. No. 62/775,473, titled "Detecting and Quantifying Liquid Pools in Hydrocarbon Fluid Pipelines" and filed Dec. 5, 2018, the entirety of which is incorporated herein by reference.

TECHNICAL FIELD

The present disclosure relates generally to systems and methods for use in a well system environment. More specifically, but not by way of limitation, this disclosure relates to detecting and quantifying liquid pools in hydrocarbon fluid pipelines.

BACKGROUND

Oil and gas pipelines can carry fluid across land and under the ocean to convey the fluid from areas of production to areas of storage and distribution. Ensuring the integrity of hundreds of kilometers of pipeline can be challenging. For natural gas pipelines, even a small pressure or temperature variation along the length can result in formation of liquid condensate and subsequent pooling in low areas within a pipeline. Liquid condensate and pooling can result in a multiphase mixture of fluids that can reduce the production or transportation capacity and efficiency of the pipelines. Water accumulation at low areas in pipelines can also lead to corrosion. The ability to monitor the pipelines for liquid accumulation can ensure uninterrupted supply of gas. But, predicting possible locations of liquid accumulation can be difficult to obtain. Moreover, it can be challenging to estimate the amount of liquid condensate in the pipeline.

DETAILED DESCRIPTION

Figure 1:
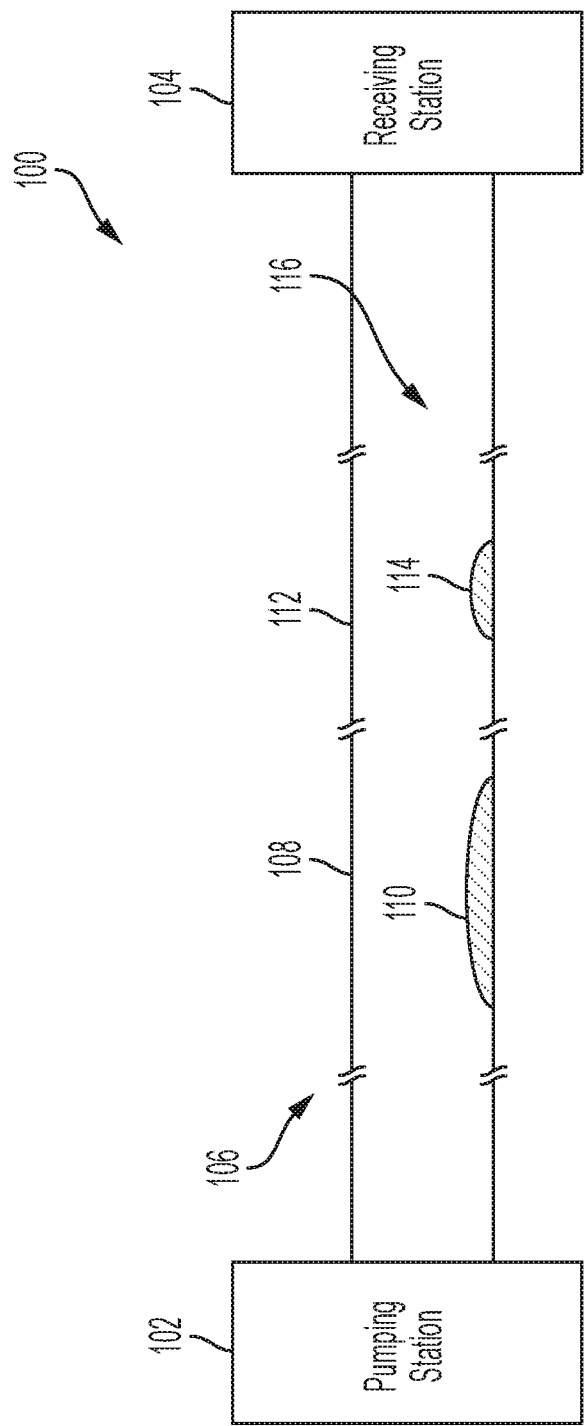
FIG. 1 is a cross-sectional view of an example of an oil and gas pipeline having liquid pools according to some aspects of the present disclosure.

Certain aspects and features relate to detecting and quantifying liquid pools in hydrocarbon fluid pipelines. Liquid pools can form in hydrocarbon fluid pipelines, reducing the total hydrocarbon flow rate. The location of liquid pooling in a gas pipeline can be predicted and the volume amount of liquid pooled can be estimated by generating a pressure wave. The pressure wave can be generated by a pressure-inducing device in line with the hydrocarbon pipeline, such as a valve, fluid-injector, or pump. The pressure-inducing device can have a pre-determined operation profile, which can be compared against a recorded pressure that is the reflection of the pressure wave against the liquid pooling at fixed locations. The recorded pressure can be analyzed to make inferences and to estimate the location and amount of pooled liquid.

Other methods of liquid detection in pipelines can involve intrusive methods such as optical measurements using special devices and can only detect liquid in flowing lines. In some examples of the present disclosure, special intrusive devices may not be required to be installed or utilized. Instead, existing pressure-inducing devices and pressure transducers installed in pipelines can be used. A pressure signal can be generated using a valve and the pressure signal can be recorded using pressure transducers. The recorded signal can be analyzed to obtain information about liquid pooling. For example, locations and volumes of the pooled liquid can be detected using the pressure signal and analyzing the reflections of this signal due to pooling in the pipeline. Pressure reflections can be computed from a possible liquid pooling location in the pipeline using a simulator.

In some examples, existing pressure-inducing devices can be used to determine the location and estimated volume of liquid pooling in a hydrocarbon pipeline. The pressure-inducing devices operating along the hydrocarbon pipeline can create a pressure wave that propagates through the fluid medium along the length of the pipe. Pressure transducers proximate to the pressure-inducing devices can measure and record the reflections of the pressure wave, or pressure fluctuations, against the liquid pooling volumes. The generated pressure wave can interact with liquid pooling volumes or other obtrusive materials accumulated along the pipeline such that the liquid pockets can modify the incident signal. Due to this interaction, the modified signal can be reflected back and recorded by the pressure transducer. In some examples, machine-learning algorithms, forward modelling, and simulations can be used to analyze the recorded pressure fluctuations to determine the location and volume of the liquid pooling.

Illustrative examples are given to introduce the reader to the general subject matter discussed here and are not intended to limit the scope of the disclosed concepts. The following describes various additional features and examples, but should not be used to limit the present disclosure.

FIG. 1 is a cross-sectional view of an oil and gas pipeline having liquid pools according to one example. Liquid condensate or pooling can occur within a hydrocarbon pipeline due to pipeline geometry. Portions of a pipeline having lower elevation with respect to portions of the pipeline having higher elevations can cause liquid pooling due to gravity. Bends or curves along the pipeline may also cause liquid pooling due to the nature of fluid flow within a non-linear pipe, such that liquid may pool at or near the change in geometry.

Liquid pooling of various volumes may occur at multiple locations along a single pipeline. For example, a pipeline pumping environment 100 can include a pumping station 102 and a receiving station 104. The pumping station 102 can pump hydrocarbon fluids along a pipeline 106 to the receiving station 104. Due to pipeline geometry, a first intermediate pipe section 108 can have a first liquid pool 110, and a second intermediate pipe section 112 can have a second liquid pool 114. Based on the pipeline geometry and other factors such as pipeline flow rate, the first liquid pool 110 and second liquid pool 114 may build up over time, causing the overall hydrocarbon flowrate to decrease. The first liquid pooling 110 and second liquid pooling 114, or any additional liquid pooling or deposited material can be at any location along the pipeline and can be of any volume.

The pipeline 106 can include multiple pressure-inducing devices and pressure transducers exiting along the pipeline 106 to detect potential liquid pooling along various portions of the pipeline 106. Determining the location and volume of liquid pooling can allow for appropriate remedial action to be taken, which can to reduce or eliminate the liquid pooling and therefore increase the hydrocarbon flow rate to a value closer or equal to an ideal hydrocarbon flowrate.

Figure 2:
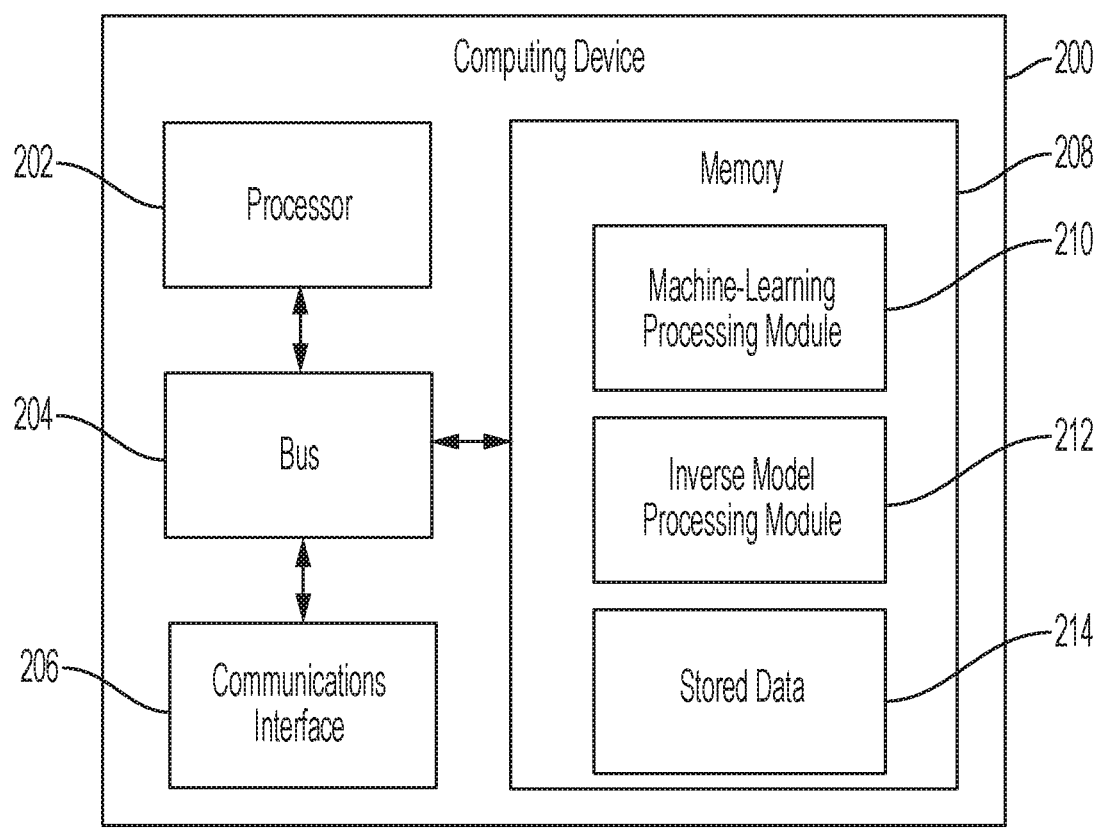
FIG. 2 is a block diagram of a computing device usable for analyzing pressure data to determine a location of pooled liquid in a pipeline according to according to some aspects of the present disclosure.

FIG. 2 is a block diagram of a computing device 200 usable for analyzing pressure data to determine a location of pooled liquid in a pipeline according to one example.

The computing device 200 can include a processor 202, a bus 204, a communications interface 206, and a memory 208. In some examples, the components shown in FIG. 2 (e.g., the processor 202, the bus 204, the communications interface 206, and the memory 208) can be integrated into a single structure. For example, the components can be within a single housing. In other examples, the components shown in FIG. 2 can be distributed (e.g., in separate housings) and in electrical communication with each other.

The processor 202 can execute one or more operations for implementing some examples of the present disclosure for detecting liquid pooling in a pipeline. The processor 202 can execute instructions stored in the memory 208 to perform the operations. The processor 202 can include one processing device or multiple processing devices. Non-limiting examples of the processor 202 include a Field-Programmable Gate Array ("FPGA"), an application-specific integrated circuit ("ASIC"), a microprocessor, etc.

The processor 202 can be communicatively coupled to the memory 208 via the bus 204. The non-volatile memory 208 may include any type of memory device that retains stored information when powered off. Non-limiting examples of the memory 208 include electrically erasable and programmable read-only memory ("EEPROM"), flash memory, or any other type of non-volatile memory. In some examples, at least some of the memory 208 can include a medium from which the processor 202 can read instructions. A computer-readable medium can include electronic, optical, magnetic, or other storage devices capable of providing the processor 202 with computer-readable instructions or other program code. Non-limiting examples of a computer-readable medium include (but are not limited to) magnetic disk(s), memory chip(s), ROM, random-access memory ("RAM"), an ASIC, a configured processor, optical storage, or any other medium from which a computer processor can read instructions. The instructions can include processor-specific instructions generated by a compiler or an interpreter from code written in any suitable computer-programming language, including, for example, C, C++, C #, etc.

The communications interface 206 can be used to communicate with the external systems or devices, such as sensors that can detect pressure fluctuations at known locations. Pressure fluctuation data received by the communications interface 206 can be transmitted to the memory 208 via the bus 204. The memory 208 can store any received pressure fluctuation data for implementing some examples. The memory 208 can store characteristics of the pressure fluctuation data and any manipulations of the pressure fluctuation data as stored data 214. The memory 208 can store pressure profile data, such as a profile representing a pressure wave generated by a pressure-inducing device, as stored data 214.

The memory 208 can include program code for a machine-learning processing module 210 and an inverse model processing module 212. The machine-learning processing module 210 can be used to identify and classify pooling or depositions based on the pressure fluctuation data. The inverse model processing module 212 can be used for estimating localized variation in pipe diameter due to pooling or deposition. The inverse model processing module 212 may also be used to convert diameter variation to equivalent liquid volumes for pooling locations to determine a range of pooling locations and volumes. In other examples, a separate processing module (not shown) in the memory 208 can determine the range of pooling locations and volumes. The range of pooling locations and volumes can be stored in stored data 214.

Figure 3:
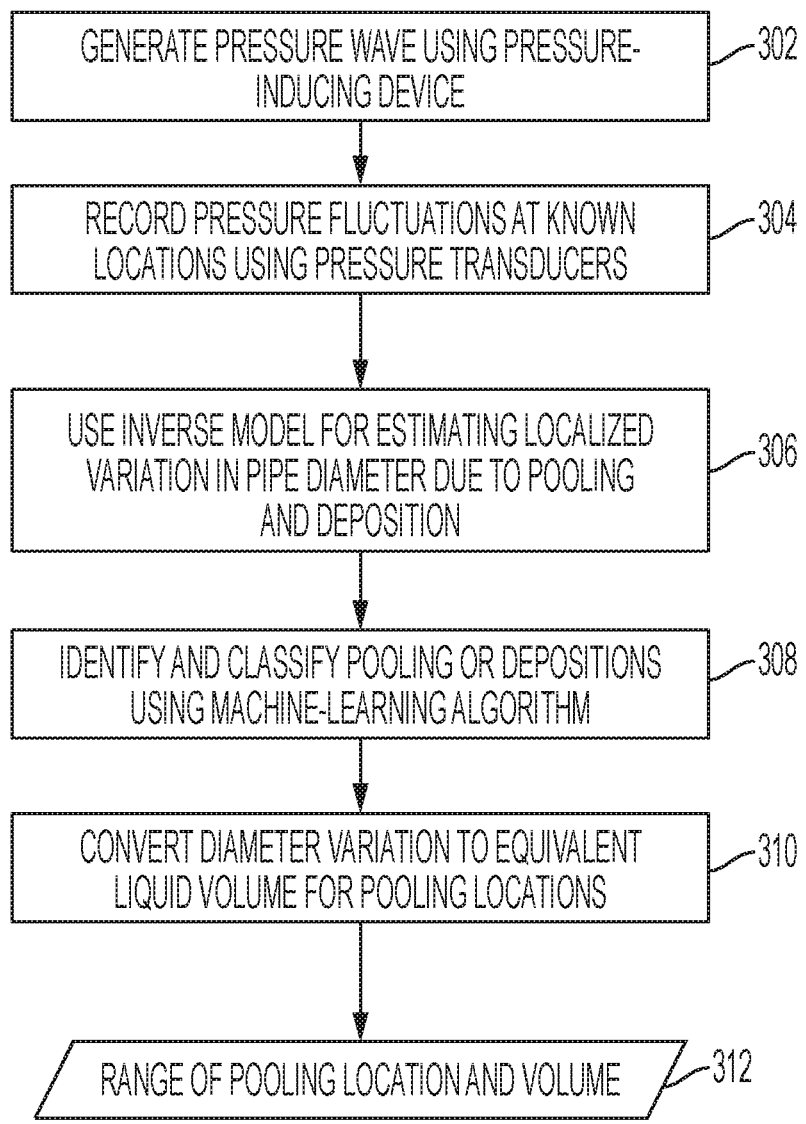
FIG. 3 is a flowchart of a process for detecting liquid pooling in a pipeline according to some aspects of the present disclosure.

FIG. 3 is a flowchart of a process for detecting liquid pooling in a pipeline according to one example of the present disclosure. Existing pressure-inducing devices and pressure transducers can be used to determine the location and volume of any liquid pooling affecting hydrocarbon flowrate along a pipeline.

In block 302, a pressure wave is generated using a pressure-inducing device. An existing device, such as a valve, fluid-injector, or pump, installed in the pipeline can create a pressure wave that propagates through the fluid medium along the length of the pipe.

In some examples, one section of the pipeline can be considered. An existing pressure-inducing device on the pipeline and a pressure transducer at a known distance from the valve can be used. A pressure pulse can be initiated by a pressure-inducing device, such as a quick operation of a valve. This operation can be complete partial or complete closure of a flowing line, or opening and closing of a static line. The resulting changes in pressure can propagate through the pipe fluid. This wave can interact with the liquid accumulated along the pipe length, which can modify the input signal generated by the pressure-inducing device. The modified signal can be reflected back and recorded by the transducer as a function of time, which can be used to construct a measured pressure profile.

Figure 4:
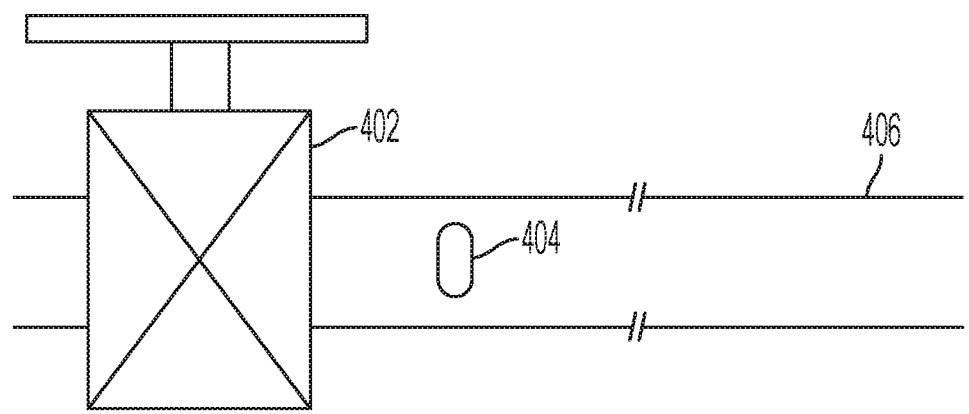
FIG. 4 is a schematic of part of a pipeline with a pressure-inducing device and a pressure transducer according to some aspects of the present disclosure.

For example, FIG. 4 is a schematic of part of a pipeline 406 with a pressure-inducing device 402 and a pressure transducer 404 according to one example of the present disclosure. As depicted in FIG. 4, the pressure-inducing device 402 is represented as a valve. In other examples, the pressure-inducing device can be a fluid-injector, pump, or other device that can control the throughput of hydrocarbons within a pipeline. FIG. 4 depicts an assembly that can implement examples as described herein. The assembly can include a portion of the pipe for carrying hydrocarbon fluid, and a pressure-inducing device positioned in the portion of the pipe to output a pressure wave in an inner area of the portion of the pipe. The assembly can further include a pressure transducer positioned in or otherwise in fluid communication with the portion of the pipe to detect pressure fluctuations of the pressure wave and output signals indicative of the pressure fluctuations to a computing device to determine a pooling or deposition location and volume in the portion of the pipe.

Figure 5:
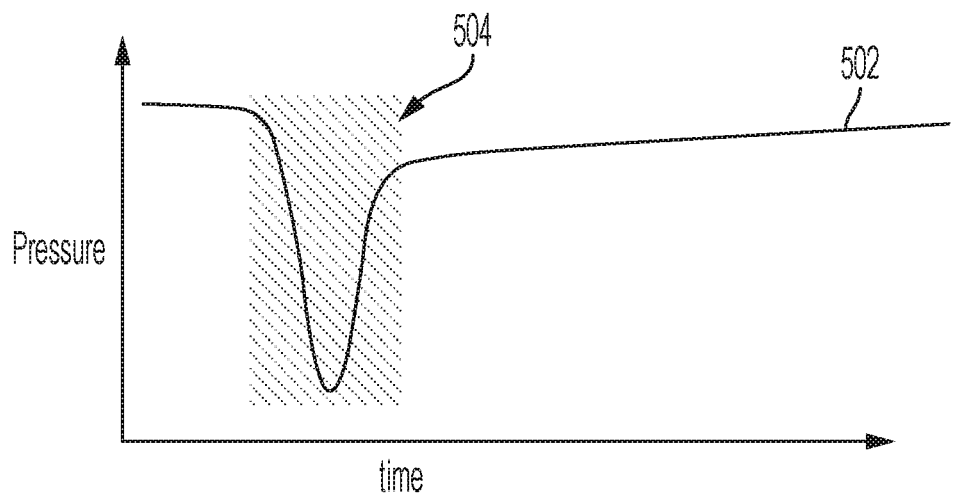
FIG. 5 is a chart showing pressure versus time relationship associated with a pressure-inducing device operation depicted in FIG. 4 according to some aspects of the present disclosure.

FIG. 5 is a chart showing pressure versus time relationship 502 associated with a pressure-inducing device operation depicted in FIG. 4 according to one example of the present disclosure.

In FIG. 4, the pressure-inducing device 402 can be located on the pipeline 406, with no pooling, and the pressure transducer 404 can be located near or proximate to the pressure-inducing device 402. In an example, near or proximate may indicate that the pressure transducer 404 is within 5 meters of the pressure-inducing device 402. Initially, the pressure-inducing device can be in a non-operative or idle state. For example, in the case where the pressure-inducing device 402 is a valve, the valve can be in a closed state. The pressure transducer 404 can record negative pressure pulses created by the pressure-inducing device 402. When the pressure-inducing device 402 is operated (e.g., the valve is opened and closed quickly within a short period of time, such as less than 500 milliseconds), the pressure-inducing device 402 can create a pressure wave similar to the one shown in FIG. 5. FIG. 5 illustrates that there can be a decrease in pressure along the pipeline 406 due to operation of the pressure-inducing device 402. For example, when the pressure-inducing device 402 is a valve, opening and then closing the valve, as depicted at pressure-inducing device profile 504 of the graph, can create a pressure fluctuation that can be used as a baseline to compare against applications in which liquid pooling is suspected.

In block 304, pressure fluctuations are recorded at known locations using pressure transducers. The location of a pressure transducer can be proximate to a corresponding pressure-inducing device. The pressure wave generated in block 302 can interact with liquid pockets accumulated along the pipeline and the liquid pockets modify the incident signal. Due to this interaction, the modified signal is reflected back and recorded by the pressure transducer.

Figure 6:
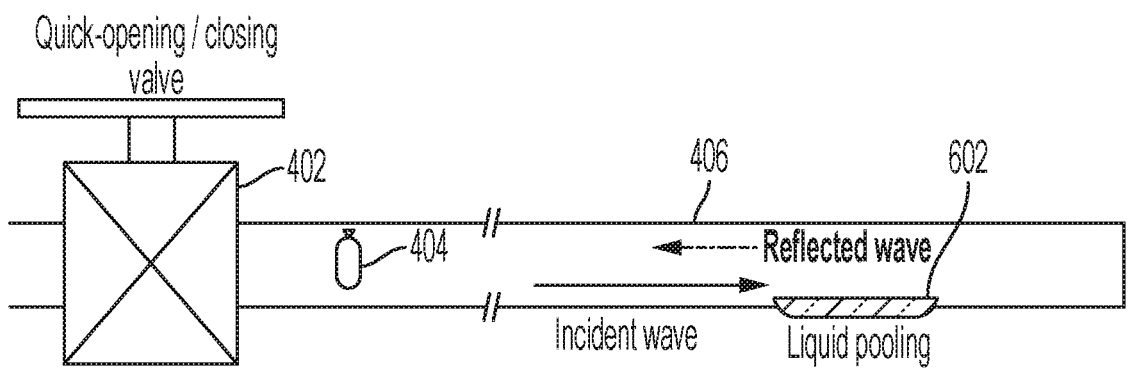
FIG. 6 is a schematic of part of a pipeline in which there is a liquid pooling location according to some aspects of the present disclosure.
Figure 7:
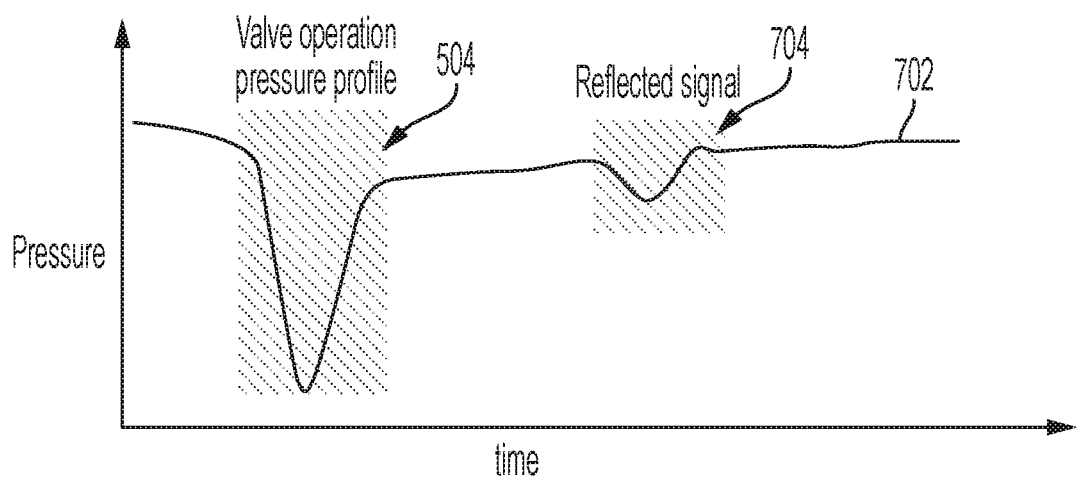
FIG. 7 is a chart showing pressure versus time relationship associated with a pressure-inducing device operation depicted in FIG. 6 according to some aspects of the present disclosure.

FIG. 6 is a schematic of part of a pipeline in which there is a liquid pooling location in the pipeline according to one example of the present disclosure. FIG. 7 is a chart showing pressure versus time relationship 702 associated with a pressure-inducing device operation depicted in FIG. 6 according to one example of the present disclosure.

The pipe material, fluid, and sound speed can be known in preparation of determining the location and volume of the liquid pooling based on the recorded pressure fluctuations. The pressure wave generated by the pressure-inducing device 402 can travel along the pipeline 406 at sound speed and can interact with liquid pooling 602. This disturbance in the signal can propagate back towards the pressure transducer 404 and can subsequently be recorded after a delay corresponding to the distance between the pressure transducer 404 and the location of the liquid pooling 602, as shown in FIG. 7.

For example, when the pressure-inducing device 402 is a valve, opening and then closing the valve, as depicted at pressure-inducing device profile 504 of the graph, can create a pressure fluctuation. The pressure fluctuation can create interact with the liquid pooling 602 to create a reflected signal profile 704. The reflected signal profile 704 can be proportional to the pressure-inducing device profile 504 based on various factors including distance from pressure-inducing device 402 and pressure transducer 404, volume of the liquid pooling 602, pressure wave speed, medium type in which the pressure wave is propagated, and any other factor that may affect recording signal speed between generation and recording.

The pressure wave signal represented by the pressure-inducing device profile 504 can be separated from the reflected signal profile 704 by subtracting the signal depicted in the pressure versus time relationship 502 from the signal depicted in the pressure versus time relationship 702. This can isolate the reflected signal caused by the liquid pooling 602. The isolated signal resulting from the comparison of recorded signals depicted in FIGS. 5 and 7 can be used as input to an inverse model.

Figure 8:
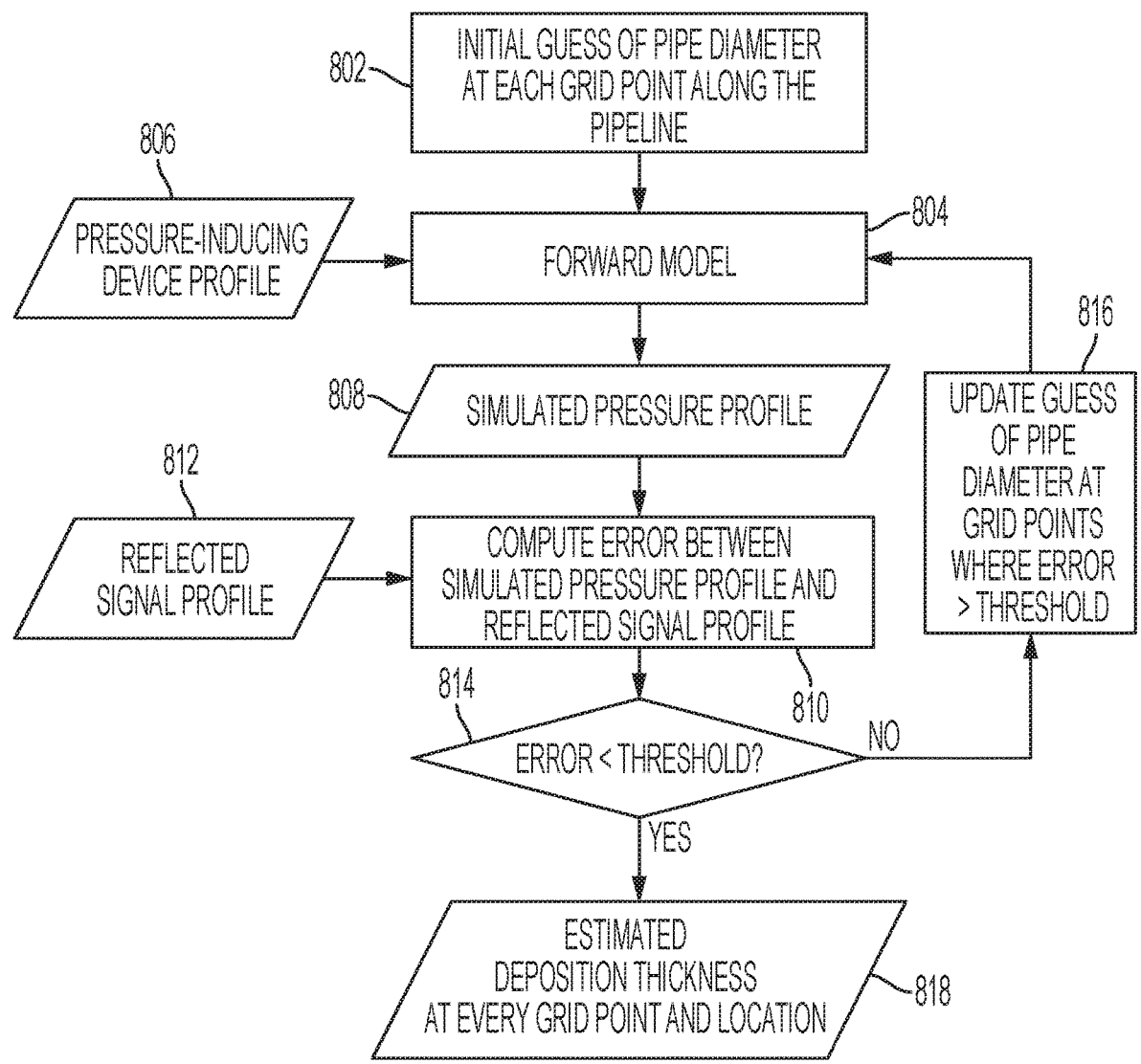
FIG. 8 is a flowchart of a pooling inversion process according to some aspects of the present disclosure.

Referring back to FIG. 3, in block 306, an inverse model is used to estimate localized variation in pipe diameter due to pooling and deposition. Based on the reflected signal profile determined in block 304, an inverse model can compute a new deposition value for each location where pooling has been recorded. The process for inverse modelling can be described with respect to FIG. 8. FIG. 8 is a flowchart of a pooling inversion process according to one example of the present disclosure.

In block 802, an initial guess of deposition at each grid point is inputted in a forward model. The guess can be based on known values for the location and diameter of a pipeline for any location of a liquid pool. For example, pipeline blueprints can include the physical specifications of a pipeline at any given location. The pipe diameter can be used to determine what percentage of that given diameter may include pooling or may otherwise be obstructed by deposited material.

In block 804, the guess of the location and volume of the liquid deposition is input into a forward model. The pressure-inducing device profile 504 in block 806 is also used as input into the forward model. The forward model can output a pressure signal for a known variation in pipe characteristics (e.g. diameter, sound-speed, density of fluid, etc.). In some examples, a forward model can be implemented through the Method of Characteristics (MOC), which can be used to solve the set of partial differential equations that describe the propagation of pressure waves in a pipe.

The forward model can be used in the pooling detection and estimation process. The forward model can describe the propagation of the pressure pulse along a pipe, upstream or downstream of a valve, including reflections from interfaces and liquid pools. The forward model can be based on MOC solutions to the set of partial differential equations that describe propagation of hydraulic transients in a pipeline. The pipeline can be divided into a fixed number (n) of sections of length $\Delta x$. The point connecting each of these grid points can be referred to as a grid point. The time for which the pressure is to be computed is also subdivided into small steps ($\Delta t$). Pressure and velocity can be computed at each of these grid points as the pressure wave propagates through the pipe until the total time is reached.

The forward model can involve the pressure-inducing device profile from block 806 and the diameter and area at each grid point being known apriori. The pressure wave can interact with the varying diameter as it propagates along the pipe from the pressure-inducing device towards the other end of the pipe. At the sections where there is a change in area from the mean pipe area, the pressure can change according to the mass and momentum conservation equations described in examples below. This reflected pressure at a fixed transducer location can be obtained as the output.

In block 808, a simulated pressure profile is determined. The simulated pressure profile can be determined from the forward model as described in block 804, which uses initial guesses of the pipe diameter and the pressure-inducing device profile as described in blocks 802 and 806 respectively.

In block 810, an error value between the simulated pressure and the reflected signal profile is computed. The reflected signal profile in block 812, representing the measured signal pressure resulting from the generated pressure wave's interaction with a liquid pool, is used as input to block 810. The along simulated pressure profile determined in block 808 is also used as input to block 810.

In block 814, the reflected signal profile and simulated pressure profile can be compared to determine an error value. If the error is greater than a set threshold, the deposition at each grid point is updated, as shown in block 816, and the forward model can again simulate pressure at each grid point in the pipe using the updated diameters. This updating process as described in blocks 804 through 816 can be repeated until the error is less than a set threshold value.

In block 818, an estimated deposition thickness at every grid point and location is output. The estimated deposition thickness can be used as input to the next process described with respect to FIG. 3. The estimated set of deposition values can be output after the error determined in block 814 is less than the set threshold value. The location of the significant depositions can be estimated based on the sound speed in the fluid medium in the pipe.

Figure 9:
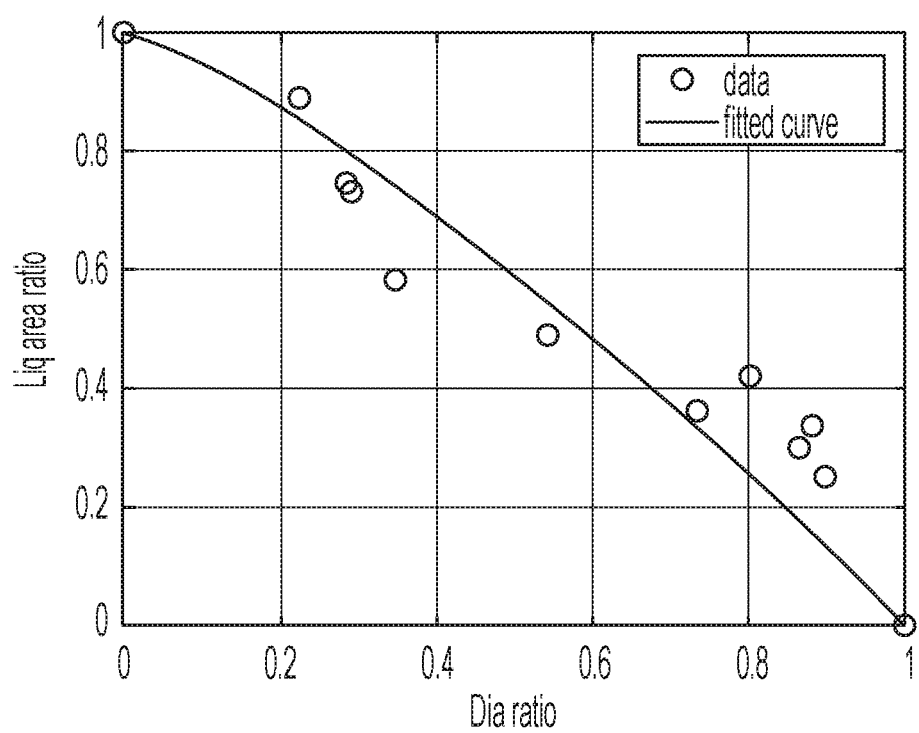
FIG. 9 is a chart of the liquid pooling area ratio versus pipeline diameter ratio relationship according to some aspects of the present disclosure.

In some examples, the estimated deposition thickness can be used to determine an empirical relationship. FIG. 9 is a chart of the liquid pooling area ratio versus pipeline diameter ratio relationship according to one example of the present disclosure. This plot shows a curve that fits to data that provided pressure reflection from a known liquid volume in the pipe. The inverse algorithm as described by FIG. 8 can used to estimate equivalent depositions causing that pressure reflection. The resulting diameter, due to liquid pooling and other material depositions, of the pipe can be the output of the inverse model.

One such empirical formula is:

$$y=ax^b+c$$

Where y is the ratio of pipe area covered by pooled liquid to the total pipe cross-sectional area. Here, x is the ratio of equivalent deposition-free diameter to the pipe diameter. Also, a, b and c are coefficients determined from the fit. Other types of equations can be obtained that fits the data set. Another example can be:

$$y=ax^2+bx+c$$

Again, a, b and c are coefficients, and x and y are as above. Yet another example of a fit can be:

$$y=a\ \sin(bx+c)$$

As before, a, b and c are coefficients, and x and y are as previously explained. There can be multiple ways to obtain data for this empirical relationship. In some examples, data for the empirical relationship can be obtained through lab experiments conducted with different pipes, fluids, pressures, and liquid pooling volumes.

Figure 10:
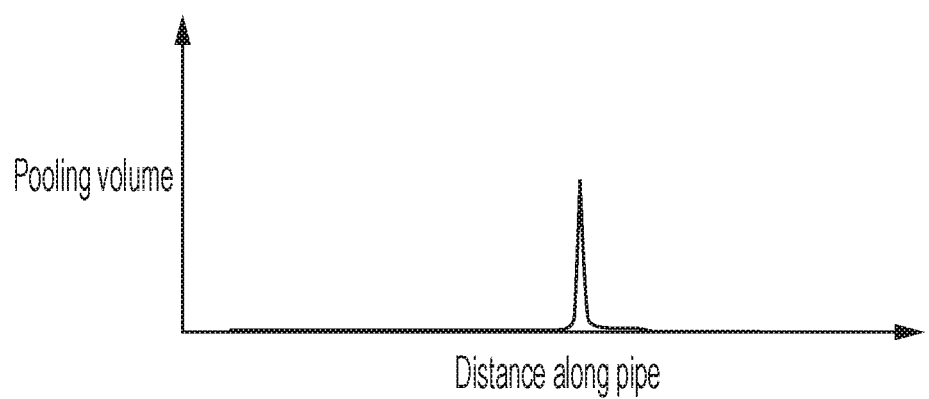
FIG. 10 is chart depicting an output of a process indicating the volume and location of pooling according to some aspects of the present disclosure.

FIG. 10 is chart depicting an output of a process, such as the process in FIG. 8, indicating the volume and location of pooling according to one example of the present disclosure. The measured pressure signal used as input to the inverse model as described in FIG. 8 can be used to compute the corresponding liquid volume and output the data, such as in chart form as shown in FIG. 10. For example, referring back to FIG. 3, the relationship and data defined by the chart in FIG. 10, which is can be the result of inverse modelling described in block 306 and FIG. 8, can be used as input to block 308. In some examples, data for the empirical relationship can be obtained through use simulations, using tools such as computation fluid dynamics (CFD). In addition, the empirical relationships can also be obtained from machine-learning processing.

In some examples, the pressure reflection from a liquid pooling volume in a pipe can be obtained using CFD simulations. A set of partial differential equations that govern the flow of fluid can be solved in a pipe geometry that has air and water at known locations initially. The Navier-Stokes equations given below describe the motion of compressible or incompressible fluids.

$$\text{Continuity: } \frac{\partial \rho}{\partial t} + \nabla \cdot (\rho u) = 0$$

$$\text{Momentum: } \frac{Du}{Dt} = -\nabla p + \nabla \cdot \tau + f.$$

Figure 11:
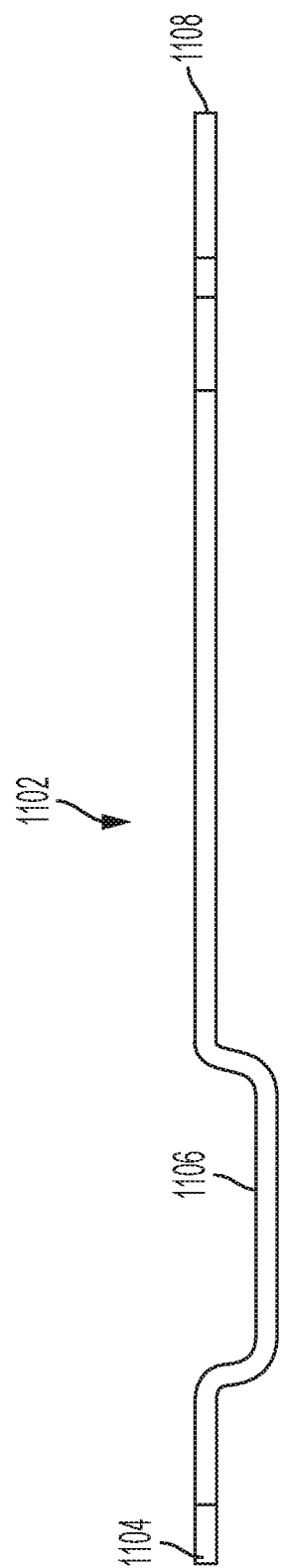
FIG. 11 is a schematic of a computational fluid dynamics (CFD) domain that can be used for gas-liquid pooling transient simulations according to some aspects of the present disclosure.

Here, u is the velocity field, p is the pressure, T is the shear stress on the fluid and f is any external force. The geometry of pipe with the fixture is shown in FIG. 11. The geometry can be first divided into a number of finite volumes referred to as computational cells and this process can be meshing the domain. A discretized form of the above equations can be solved over each of these elements numerically. Simulations such as these involve geometries that can contain hundreds of thousands, or even millions of computational cells.

FIG. 11 is a schematic of a CFD domain 1102 that can be used for gas-liquid pooling transient simulations according to one example of the present disclosure. FIG. 11 can include a fixture 1106 at which liquid is pooled. At the boundaries 1104, 1108, a known pressure variation can be input and the corresponding pressure and velocity in each of the computational cell can be computed at discrete time steps, up to a required time. The pressure wave can traverse along the pipe, interact and/or reflect with the fixture and its liquid content. The reflected pressure can be measured at a known location, similar to a pressure transducer in a real world pipeline environment. The input pressure wave can be subtracted from the measured signal and the remaining signal can be the reflection from the liquid pooling in the fixture 1106.

Figure 12:
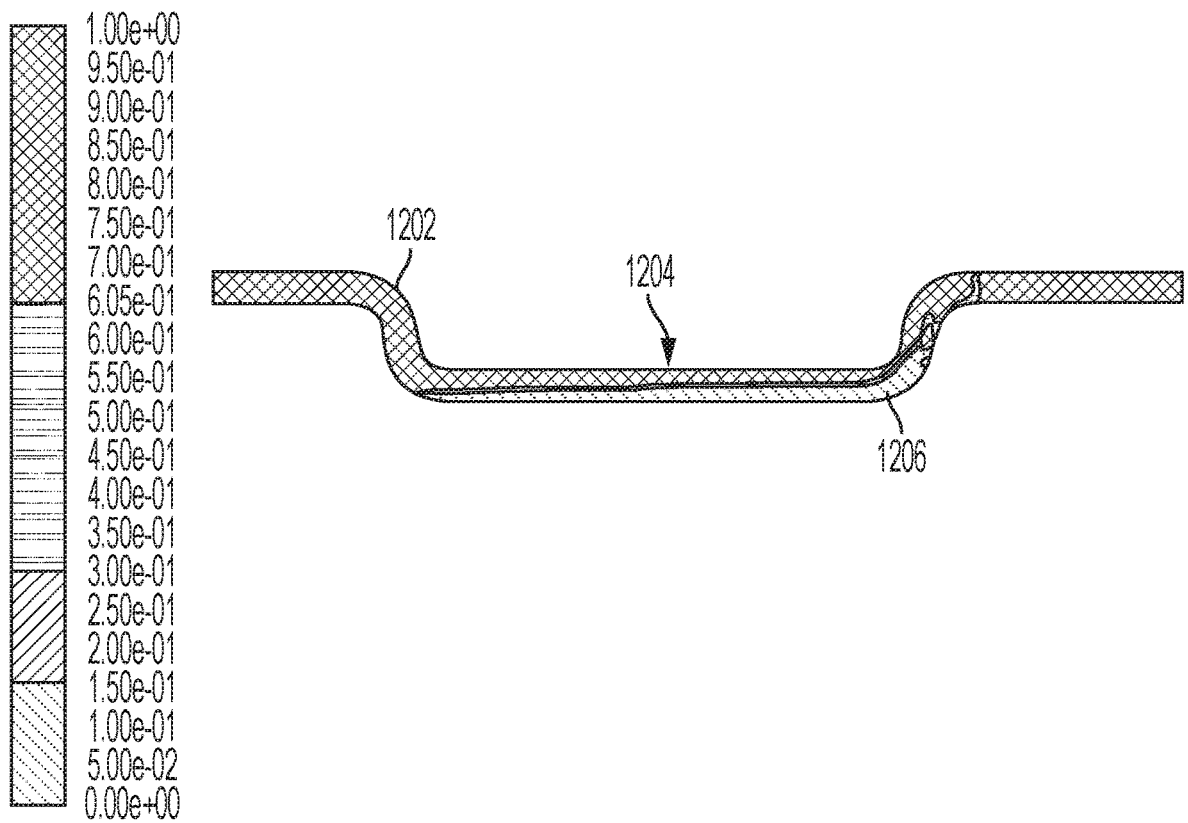
FIG. 12 shows a CFD simulation of water sloshing in the fixture of FIG. 11 and a known input pressure profile according to some aspects of the present disclosure.

FIG. 12 shows a CFD simulation of water sloshing in the fixture of FIG. 11 and a known input pressure profile according to one example of the present disclosure. The pipeline 1202 can include a fixture 1204 having a nonlinear geometry where liquid pooling is likely to occur. Sloshing water 1206 in the fixture 1204 can be observed due to passing of the pressure pulse (not shown) over the liquid surface. The CFD method can provide detailed pressure and velocity information in the entire modeled geometry of the pipeline 1202. But, if the pressure transducer is located at a great distance (e.g., kilometers) away from the liquid pooling location including the sloshing water 1206, CFD simulation may not be directly applied to generate data at that location because simulating a very long pipeline may be cost prohibitive. To overcome this issue, the reflection signal can be propagated to a desired distance using the 1D forward model to account for pressure losses, but with no liquid pooling in between the CFD measurement location and the physical transducer location. The 1D model can simulate pressure at the desired location within a fraction of the computational cost. This method can be used to generate various different scenarios of pressure-inducing device inputs and corresponding reflections using CFD. These reflections can be propagated to desired transducer locations.

Figure 13:
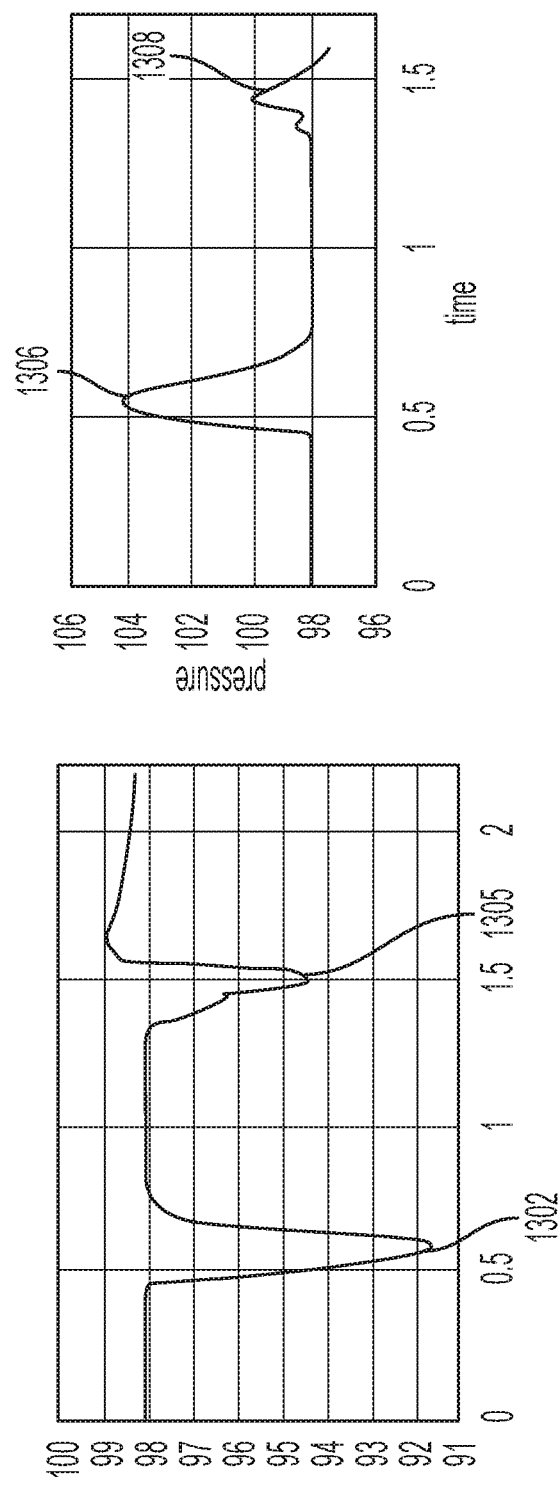
FIG. 13 shows two different pressure-inducing device input signals and the resulting CFD generated reflection signals according to some aspects of the present disclosure.

FIG. 13 shows two different pressure-inducing device input signals and the resulting CFD generated reflection signals according to one example of the present disclosure. The sample charts depict pressure values with respect to time of the generated input pulses 1302, 1306 and resulting respective reflected signals 1304, 1308.

Referring back to FIG. 3, in block 308, liquid pooling or depositions are identified and classified using a machine-learning algorithm. The signal derived from block 306, resulting in the data depicted in FIG. 310, can be used as input to a machine-learning algorithm of a computing device to distinguish between various scenarios for each data point or location—neither pooling or deposition, pooling, or deposition. The location of liquid pools and deposition can be computed based on the time of reflected signal and the speed of sound in the fluid. Also, the magnitude of the reflected signal can depend on the volume of liquid.

Initially, from the data corresponding to a liquid pool determined in block 306, the machine-learning processing module can extract the features in frequency domain, and information about the location of pooling or deposition. Based on these features, the machine-learning processing module can further classify the data points into pooling or deposition. For example, liquid pooling may have different characteristics than liquid or material deposition, such that effective fluid flow rates caused by pooling of a certain volume may be different from effective fluid flow rates for depositions having the same volume.

Machine-learning models can involve using a number of data points to train the model and then validate it using separate data points. Once the model is developed, it can be tested using new data sets. The machine-learning model can be trained using a particular set of 'features' that it can use to classify a new input data set. These features can be picked carefully, depending on the physical nature of the problem as well as the data set.

In one example, the machine-learning model can be taught using the following features:
initial_pulse_duration: The time duration of the pulse.
Shape of the pulse—as captured using a fast Fourier transform (FFT), for example.
Spectrum of the measurement, using an FFT, for example.
Energy in each frequency bin in the spectrum.
initial_pulse_slope_min: Slope of the best fit line of 500 points (1/10th of a second) that is minimum.
initial_pulse_slope_max: Slope of the best fit line of 500 points (1/10th of a second) that is maximum.
initial_pulse_bwfilter_min: the minimum Butterworth value standardized by mean and standard deviation of the entire pulse.
Dip is identified as the region where the slope is continuously negative for the longest duration. Slope is of the best fit line of 500 points (1/10th of a second).
dip_bwfilter_min: the minimum Butterworth value.
dip_duration: The duration for which the slope is negative.
dip_fitted_min: minimum fitted value of the 500th point in the region where the slope is negative for the longest period standardized by mean and standard deviation of the entire pulse.
dip_slope_min: minimum slope of the best fit line in the region where the slope is negative for the longest period of time.

In some examples, the classification algorithm referred to as Random Forest model, as well as a neural network model, can be tested and applied. Both models can provide reasonable and approximately equal accuracy on the tested data.

In response to detecting that the pipeline is experiencing either pooling or deposition, the machine-learning model can be used to distinguish between the two. The frequency domain plots of deposition and pooling using FFT method can be used to determine the features. To capture this distinction, five energy bins can be as input variables to ML model. These variables can be calculated by first transforming from pressure pulse variable in frequency domain. Then, the frequency interval between 5-100 can be used by scaling the values by the maximum frequency. In some examples, the following frequency bins (in Hz) can be used:
1) 5-10,
2) 10-20,
3) 20-30,
4) 30-40,
5) 40-50

Trapezoidal Integration can be used to perform integration on given frequency intervals to calculate energy in these bins. This can be performed using the formula below:

$$\int A^2 df$$

Where 'A' is amplitude and T is the frequency.

The data can be normalized prior to executing the machine-learning module, by using min-max scaling according to the following relationship.

$$z = \frac{x - \min(x)}{\max(x) - \min(x)}$$

Figure 14:
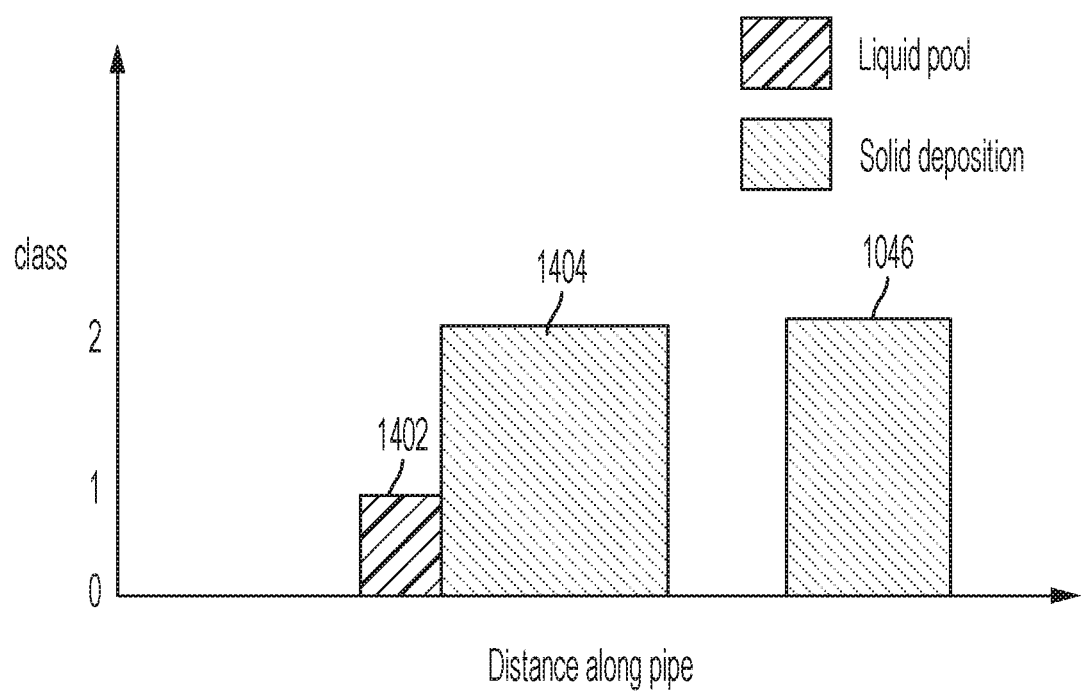
FIG. 14 depicts an example of the graphical output of a machine-learning model for classifying obstructions within a hydrocarbon pipeline according to some aspects of the present disclosure.

A rolling window of some fixed length may be used to compute the spectrum of the data for classification within that window. The output of the machine learning algorithm can be a class identifier (such as 0—for no liquid or solid, 1—for liquid, 2—for solid) as a function of distance along the pipe. FIG. 14 depicts an example of the graphical output of a machine-learning model for classifying obstructions within a hydrocarbon pipeline according to one example of the present disclosure. For example, one portion, or grid, of the pipeline can include an initial liquid pooling 1402, followed by additional grid locations along the distance of the pipe having obstructions 1404, 1406 classified as solid depositions.

Although an Artificial Neural Network machine-learning model to classify pooling and deposition cases is described, other machine-learning models can also be used. Artificial neural networks can be deep learning techniques, inspired by biological neural networks (central nervous systems, such as the brain). These networks can be represented as systems of interconnected "neurons," which send messages to each other. The connections within the network can be systematically adjusted based on inputs and outputs, making them useful for supervised learning.

Figure 15:
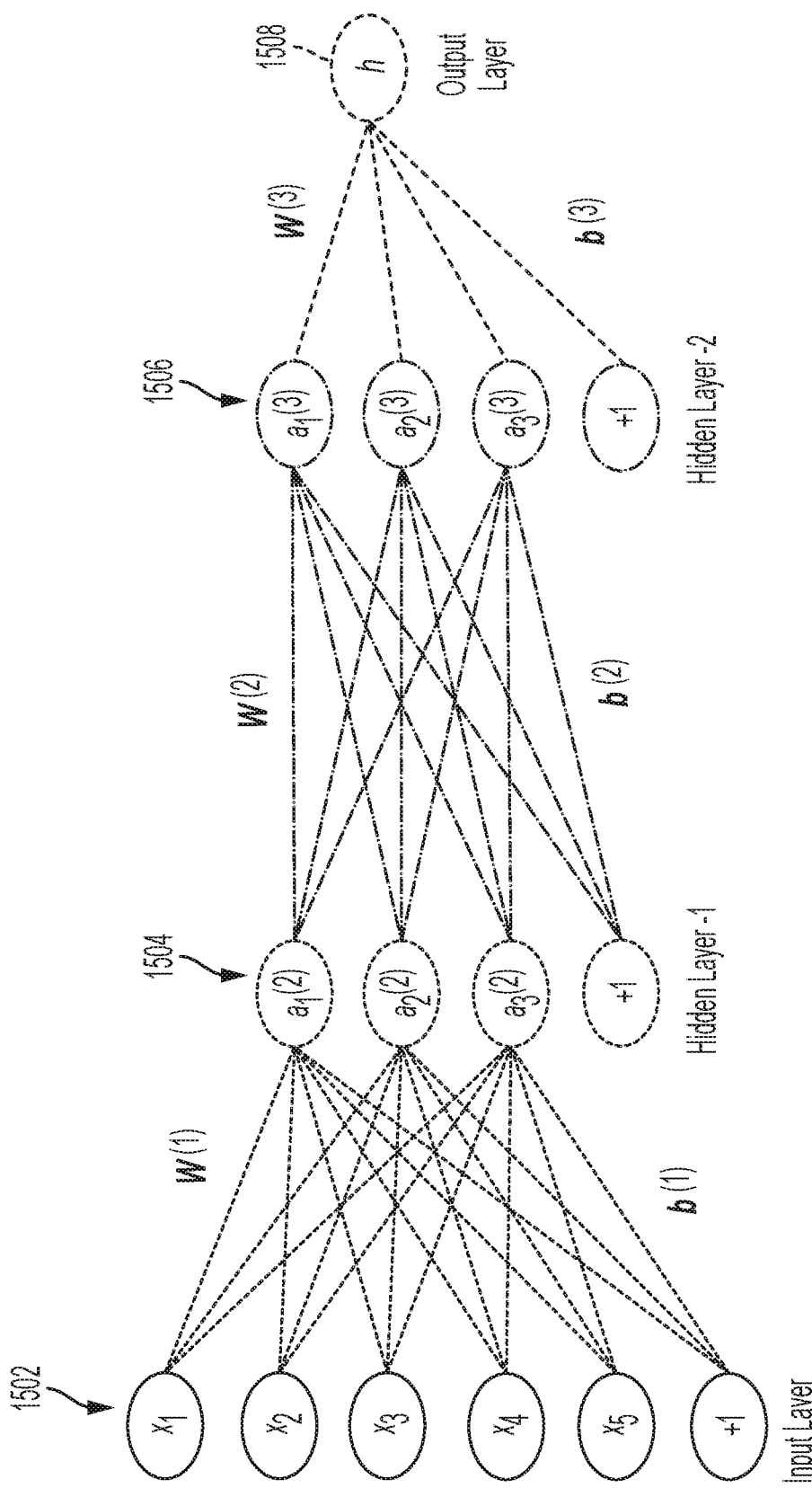
FIG. 15 shows a representation of a neural network that can be used to classify pooling and deposition according to some aspects of the present disclosure.

FIG. 15 shows a representation of a neural network that can be used to classify pooling and deposition according to one example of the present disclosure. The circles in FIG. 15 can represent neurons and the lines can represent synapses. Synapses can take the input 1502 and multiply it by a "weight" (the "strength" of the input in determining the output) and add bias for each neuron. Neurons can add the outputs from the synapses and apply an activation function. Training a neural network involves calibrating the "weights" by repeating two steps: forward propagation and back propagation.

In forward propagation, a set of weights (e.g., W1, W2, W3) can be applied to the input data to calculate an output. These weights can be selected randomly based on Gaussian distribution during a first iteration that forward propagation is performed. The product of the inputs is summed with their corresponding set of weights to arrive at the first values for the hidden layers 1504, 1506. To get the final value at output 1508, the activation function is applied to the hidden layer 1504, 1506 sums. The purpose of the activation function is to transform the input signal into the output 1508. The activation function can be useful for neural networks to model complex non-linear patterns that simpler models might miss.

In back propagation, the margin of error of the output 1508 can be measured and the weights can be adjusted accordingly to decrease the error. Neural networks can repeat both forward and back propagation until the weights are calibrated to accurately predict the output 1508.

Data normalization can be used as a pre-processing step to rescale values to fit in a specific range to assure better convergence for artificial neural network processing. For example, the artificial neural network model can be built on data using five input variables, two hidden layers, and one output layer with twenty-eight neurons on each hidden layer, as exemplified in FIG. 15.

In some examples, 'RELU' (Rectified Linear Unit) activation function can be used to provide improvement in convergence from any other function. RELU can avoid and rectify a vanishing gradient problem. The function can be used for hidden layer and "sigmoid" loss function for output layer. An "Adam" Optimizer can be used to compile the artificial neural network model based on accuracy metric.

In some examples, the processes described in blocks 306 and 308 can be performed in any order. For example, the processes described in block 306 can be implemented to estimate localized variation in pipe diameter, which can then be used as inputs (e.g., nodal inputs) to the machine-learning described in block 308. Alternatively, pooling can be identified and classified as described in block 308, which can then be used as input to the inverse modelling described in block 306. In some examples, the processes described in blocks 306 and 308 can be implemented simultaneously, such that outputs from the inverse modelling and machine-learning algorithm can be continuously used as inputs to each process.

Referring back to FIG. 3, in block 310, diameter variation for pooling locations, based on the outputs from blocks 306 and 308, is converted to equivalent liquid volume. The computed depositions can be converted to an equivalent volume using a correlation developed from experimental data and simulations. This conversion can be implemented using a look-up table or an empirical formula. The converted volumes derived from the output of block 306 may be different depending on whether the volume has been classified as a liquid pool or material deposit, as described in block 308. Further, the diameters can be converted to an equivalent liquid or solid volume at each grid point based on a correlation that has been developed from the described examples.

In block 312, the range of liquid or solid pooling location and volume is output. The converted volume determined in block 310 can be output by a computing device to a display device or another system that may utilize the information to perform or initiate a remedial process to alter or alleviate the obstruction caused by the pooling or deposition. For example, the converted volume may be output to a display device to instruct an operator to shift or repair a grid or portion of the pipeline, such that the pipeline geometry can be reconfigured to remove or alleviate liquid pooling or solid deposition areas.

Figure 16:
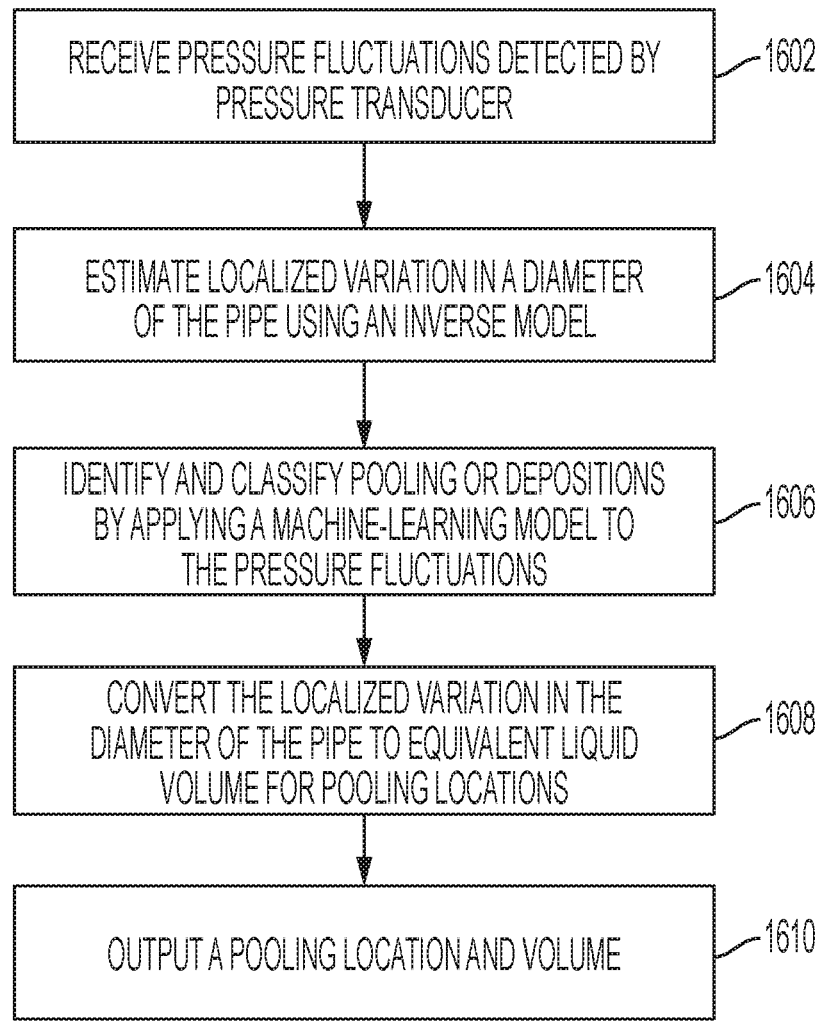
FIG. 16 is a flowchart of a computer-implemented process for detecting and quantifying liquid pools in hydrocarbon fluid pipelines according to some aspects of the present disclosure.

FIG. 16 is a flowchart of a process for detecting and quantifying liquid pools in hydrocarbon fluid pipelines according to one example. Other examples can include more steps, fewer steps, different steps, or a different order of the steps described with respect to FIG. 16. For example, the processes described in blocks 304 and 306 can be implemented in any order, where the output of the first implemented block of either 304 or 306 can be used as inputs to the second implemented block. The steps of FIG. 16 are described with reference to components discussed in FIG. 2. Some or all of the steps shown in FIG. 16 can be implemented using the computing device 200 of FIG. 2.

In block 1602, pressure fluctuations detected by a pressure transducer are received. The pressure transducer can be in a pipe for carrying hydrocarbon fluid. The pressure fluctuations can be the result of a pressure-inducing device located within the pipe, where the pressure-inducing device can be operable to output a pressure signal. The pressure fluctuations can be the signals reverberated against obstructions in the pipe, such as liquid pooling or material deposits, in response to the pressure signal, or wave, generated by the pressure-inducing device. The pressure transducers can measure the magnitude of the pressure fluctuations, where the magnitude, and time between pressure signal generation and pressure fluctuation measurement, can be used to determine a location and volume of the liquid pooling or solid deposition.

In some examples, a computing device can transmit a signal or command to the pressure-inducing device to cause the pressure-inducing device to generate the pressure signal. The command can be executed automatically according to a test plan or experiment executed by the computing device. In some examples, the computing device can receive a command from a pipeline engineer or operator instructing the computing device to transmit the command signal to the pressure-inducing device.

In some examples, the pressure-inducing device can be a valve, a fluid-injector, a pump, or any other device capable of propagating a pressure signal within a fluid environment. In some example, the pressure transducer can be located proximate to the pressure-inducing device. Positioning the pressure transducer near the pressure-inducing device can reduce the amount of error correction needed to determine a time-dependent relationship between the pressure signal and the measured pressure fluctuations. For example, measuring pressure fluctuations using a pressure transducer that is a significant distance from the pressure-inducing device can require distance correction to ensure that the time between pressure signal generation and pressure fluctuation detection accounts for the variation in distance. Comparatively, measuring pressure fluctuations using a pressure transducer that is proximate to the pressure-inducing device can reduce or eliminate the error correction with respect to distance, since both devices are located at a same or nearly the same distance from a liquid pool or material deposit.

In block 1604, a localized variation in a diameter of the pipe is estimated using an inverse model. The inverse model can be implemented according to example, including the processes described in FIG. 8. The localized variation in a diameter of the pipe can be referred to as an effective diameter of the pipe. In this regard, a portion of the diameter can include liquid pooling or material deposition that can obstruct the portion of the pipe. Thus, the localized variation in the diameter of the pipe can be an effective diameter of the pipe, such that hydrocarbon flow can only propagate through the effective diameter of the pipe. The localized variation in the diameter of the pipe can be measured as a distance between a surface of the pooling or deposition and a surface of an opposite end of the pipe.

In some examples, inverse modelling can be include generating an estimated value of the localized variation in the diameter of the pipe, and generating a simulated pressure profile using a forward model based on the pressure signal and estimated value of the localized variation in the diameter of the pipe, as described in some examples. The inverse model can include steps of determining an error value between the simulated pressure profile and the pressure fluctuations as described in some examples. The inverse modelling can further include updating the forward model with an updated estimated value of the localized variation in the diameter of the pipe and repeating the steps of generating an estimated value, generating a simulated pressure profile, and determining an error value until the error value is below a threshold value. Updating the forward model of the inverse modelling can allow the inverse model to more accurately estimate the localized variation in the effective diameter of the pipe caused by any liquid pooling or material deposition present.

In block 1606, pooling or depositions are identified and classified by applying a machine-learning model to the pressure fluctuations. The machine-learning model can classify any identified obstructions within a pipe as either a liquid, solid, or other type of material, as described by some examples.

In block 1608, the localized variation in the diameter of the pipe is converted to an equivalent liquid volume for pooling locations. The identified and classified pooling or depositions determined in block 1606 can be converted to an equivalent volume using a correlation developed from experimental data or simulations. This conversion can be implemented using a look-up table or an empirical formula. The diameters can be converted to an equivalent liquid or solid volume at each grid point based on a correlation that has been developed as described in some examples.

In block 1610, a pooling or deposition location and volume is output. The location and volume of the liquid pooling or material deposition that is output can be used to determine a remedial action on the pipe to remove or reduce the pooling or deposition. The computing device can output the pooling or deposition location and volume to a display device or another system that may utilize the information (e.g., data logs) to perform or initiate a remedial process to alter or alleviate the obstruction caused by the pooling or deposition. For example, the converted volume may be output to a display device to instruct an operator to shift or repair a grid or portion of the pipeline, such that the pipeline geometry can be reconfigured to remove or alleviate liquid pooling or solid deposition areas.

In some examples, the computing device can analyze the pooling or deposition location and volume to determine a command instruction for initiating a remedial action, which can be output to a display device or other systems individually or along with the location and volume of the deposition. The computing device can analyze the location and volume of the pooling or deposition, along with known physical characteristics of the pipeline, to determine a remedial action to output. For example, the computing device can have data stores including physical characteristics of the pipeline, such as location, diameter, geometry, and elevation. Using these physical characteristics, the computing device can determine, based on the volume and location determined in block 1608, and output an appropriate remedial instruction to cause an action such as raising a portion of a pipeline to a higher elevation, adjusting hydrocarbon throughout, or instruction a portion of the pipeline be repaired, replaced, or cleaned.

In some aspects, systems, devices, and methods for detecting and quantifying liquid pools in hydrocarbon fluid pipelines are provided according to one or more of the following examples:

Example 1 is an assembly comprising: a pipe for carrying hydrocarbon fluid; a pressure-inducing device positioned in a portion of the pipe to output a pressure wave in an inner area of the portion of the pipe; and a pressure transducer in fluid communication with the portion of the pipe to detect pressure fluctuations of the pressure wave and output a signal indicative of the pressure fluctuations to a computing device that determines (i) a pooling or deposition location and (ii) a volume in the portion of the pipe.

Example 2 is the assembly of example 1, wherein the signal indicative of the pressure fluctuations is usable by the computing device to determine the pooling or deposition location and to determine volume in the portion of the pipe by: estimating a localized variation in a diameter of the pipe caused by pooling or deposition using an inverse model; identifying and classifying pooling or depositions by applying a machine-learning model to the pressure fluctuations; converting the localized variation in the diameter of the pipe to equivalent liquid volume for pooling locations; and outputting the pooling or deposition location and volume that is usable for determining an action on the pipe to remove the pooling or deposition.

Example 3 is the assembly of example 2, wherein the inverse model is usable to estimate, by the computing device, the localized variation in the diameter of the pipe caused by pooling or deposition by: generating an estimated value of the localized variation in the diameter of the pipe;

generating a simulated pressure profile using a forward model based on the pressure wave and estimated value of the localized variation in the diameter of the pipe; determining an error value between the simulated pressure profile and the pressure fluctuations; and updating the forward model with an updated estimated value of the localized variation in the diameter of the pipe and repeating the steps of generating the estimated value, generating the simulated pressure profile, and determining the error value until the error value is below a threshold value.

Example 4 is the assembly of examples 1-3, wherein the pressure-inducing device comprises a valve, a fluid-injector, or a pump.

Example 5 is the assembly of examples 1-4, wherein the pressure transducer is positioned proximate to the pressure-inducing device.

Example 6 is the assembly of examples 1-5, wherein the pressure fluctuations result from an interaction of the pressure wave against a pooling liquid volume at the pooling or deposition location.

Example 7 is a non-transitory computer-readable medium including program code that is executable by a processing device for causing the processing device to: receive a signal indicative of pressure fluctuations detected by a pressure transducer in a pipe for carrying hydrocarbon fluid in response to a pressure-inducing device of the pipe outputting a pressure signal; estimate a localized variation in a diameter of the pipe caused by a pooling or deposition using an inverse model; identify and classify the pooling or deposition by applying a machine-learning model to the pressure fluctuations; convert the localized variation in the diameter of the pipe to equivalent liquid volume for pooling locations; and output (i) a pooling or deposition location and (ii) a volume that are usable for determining an action on the pipe to remove the pooling or deposition.

Example 8 is the non-transitory computer-readable medium of example 7, wherein the non-transitory computer-readable medium includes program code that is executable by the processing device for causing the processing device to estimate the localized variation in the diameter of the pipe caused by the pooling or deposition using the inverse model by: generating an estimated value of the localized variation in the diameter of the pipe; generating a simulated pressure profile using a forward model based on the pressure signal and estimated value of the localized variation in the diameter of the pipe; determining an error value between the simulated pressure profile and the pressure fluctuations; and updating the forward model with an updated estimated value of the localized variation in the diameter of the pipe and repeating the steps of generating the estimated value, generating the simulated pressure profile, and determining the error value until the error value is below a threshold value.

Example 9 is the non-transitory computer-readable medium of examples 7-8, wherein the non-transitory computer-readable medium includes program code that is executable by the processing device for causing the processing device to: transmit a command to the pressure-inducing device to cause the pressure-inducing device to generate the pressure signal, wherein the pressure fluctuations detected by the pressure transducer are signal reflections of the pressure signal.

Example 10 is the non-transitory computer-readable medium of examples 7-9, wherein the pressure transducer is located proximate to the pressure-inducing device.

Example 11 is the non-transitory computer-readable medium of examples 7-10, wherein the non-transitory computer-readable medium includes program code that is executable by the processing device for causing the processing device to: classify the pooling or deposition at the pooling or deposition location as a liquid or a solid.

Example 12 is the non-transitory computer-readable medium of examples 7-11, wherein the pressure-inducing device comprises a valve, a fluid-injector, or a pump.

Example 13 is the non-transitory computer-readable medium of examples 7-12, wherein the localized variation in the diameter of the pipe is measured as a distance between a surface of the pooling or deposition and a surface of an opposite end of the pipe.

Example 14 is a computer-implemented method comprising: receiving pressure fluctuations detected by a pressure transducer in a pipe for carrying hydrocarbon fluid in response to a pressure-inducing device of the pipe outputting a pressure signal; estimating a localized variation in a diameter of the pipe caused by pooling or deposition using an inverse model; identifying and classifying the pooling or deposition by applying a machine-learning model to the pressure fluctuations; converting the localized variation in the diameter of the pipe to equivalent liquid volume for pooling locations; and outputting (i) a pooling or deposition location and (ii) outputting a volume that are usable for determining an action on the pipe to remove the pooling or deposition.

Example 15 is the computer-implemented method of example 14, further comprising: transmitting a command to the pressure-inducing device to cause the pressure-inducing device to generate the pressure signal, wherein the pressure fluctuations detected by the pressure transducer are signal reflections of the pressure signal.

Example 16 is the computer-implemented method of examples 14-15, wherein estimating the localized variation in the diameter of the pipe caused by the pooling or deposition using the inverse model further comprises: generating an estimated value of the localized variation in the diameter of the pipe; generating a simulated pressure profile using a forward model based on the pressure signal and estimated value of the localized variation in the diameter of the pipe; determining an error value between the simulated pressure profile and the pressure fluctuations; and updating the forward model with an updated estimated value of the localized variation in the diameter of the pipe and repeating the steps of generating the estimated value, generating the simulated pressure profile, and determining the error value until the error value is below a threshold value.

Example 17 is the computer-implemented method of examples 14-16, wherein the pressure transducer is located proximate to the pressure-inducing device.

Example 18 is the computer-implemented method of examples 14-17, wherein the localized variation in the diameter of the pipe is measurable as a distance between a surface of the pooling or deposition and a surface of an opposite end of the pipe.

Example 19 is the computer-implemented method of examples 14-18, wherein classifying the pooling or deposition includes classifying the pooling or deposition as a liquid or a solid.

Example 20 is the computer-implemented method of examples 14-19, wherein the pressure-inducing device comprises a valve, a fluid-injector, or a pump.

The foregoing description of certain embodiments, including illustrated embodiments, has been presented only for the purpose of illustration and description and is not intended to be exhaustive or to limit the disclosure to the precise forms disclosed. Numerous modifications, adaptations, combinations, and uses thereof are possible without departing from the scope of the disclosure.

What is claimed is:

1. An assembly comprising:
a pipe for carrying hydrocarbon fluid;
a pressure-inducing device positioned in a portion of the pipe to output a pressure wave in an inner area of the portion of the pipe; and
a pressure transducer in fluid communication with the portion of the pipe to detect pressure fluctuations of the pressure wave and output a signal indicative of the pressure fluctuations to a computing device that determines (i) a pooling or deposition location and (ii) a volume in the portion of the pipe, the computing device including program code that is executable by a processing device for causing the processing device to:
estimate a localized variation in a diameter of the pipe caused by a pooling or deposition using an inverse model;
identify and classify the pooling or deposition by applying a machine-learning model to the pressure fluctuations; and
convert the localized variation in the diameter of the pipe to equivalent liquid volume for pooling locations.

2. The assembly of claim 1, wherein the signal indicative of the pressure fluctuations is usable by the computing device to:
output the pooling or deposition location and volume that is usable for determining an action on the pipe to remove the pooling or deposition.

3. The assembly of claim 1, wherein the inverse model is usable to estimate, by the computing device, the localized variation in the diameter of the pipe caused by pooling or deposition by:
generating an estimated value of the localized variation in the diameter of the pipe;
generating a simulated pressure profile using a forward model based on the pressure wave and estimated value of the localized variation in the diameter of the pipe;
determining an error value between the simulated pressure profile and the pressure fluctuations; and
updating the forward model with an updated estimated value of the localized variation in the diameter of the pipe and repeating the steps of generating the estimated value, generating the simulated pressure profile, and determining the error value until the error value is below a threshold value.

4. The assembly of claim 1, wherein the pressure-inducing device comprises a valve, a fluid-injector, or a pump.

5. The assembly of claim 1, wherein the pressure transducer is positioned proximate to the pressure-inducing device.

6. The assembly of claim 1, wherein the pressure transducer is configured to detect the pressure fluctuations corresponding to an interaction of the pressure wave against a pooling liquid volume at the pooling or deposition location.

7. A non-transitory computer-readable medium including program code that is executable by a processing device for causing the processing device to:
receive a signal indicative of pressure fluctuations detected by a pressure transducer in a pipe for carrying hydrocarbon fluid in response to a pressure-inducing device of the pipe outputting a pressure signal;
estimate a localized variation in a diameter of the pipe caused by a pooling or deposition using an inverse model;
identify and classify the pooling or deposition by applying a machine-learning model to the pressure fluctuations;
convert the localized variation in the diameter of the pipe to equivalent liquid volume for pooling locations; and
output (i) a pooling or deposition location and (ii) a volume that are usable for determining an action on the pipe to remove the pooling or deposition.

8. The non-transitory computer-readable medium of claim 7, wherein the non-transitory computer-readable medium includes program code that is executable by the processing device for causing the processing device to estimate the localized variation in the diameter of the pipe caused by the pooling or deposition using the inverse model by:
generating an estimated value of the localized variation in the diameter of the pipe;
generating a simulated pressure profile using a forward model based on the pressure signal and estimated value of the localized variation in the diameter of the pipe;
determining an error value between the simulated pressure profile and the pressure fluctuations; and
updating the forward model with an updated estimated value of the localized variation in the diameter of the pipe and repeating the steps of generating the estimated value, generating the simulated pressure profile, and determining the error value until the error value is below a threshold value.

9. The non-transitory computer-readable medium of claim 7, wherein the non-transitory computer-readable medium includes program code that is executable by the processing device for causing the processing device to:
transmit a command to the pressure-inducing device to cause the pressure-inducing device to generate the pressure signal, wherein the pressure fluctuations detected by the pressure transducer are signal reflections of the pressure signal.

10. The non-transitory computer-readable medium of claim 7, wherein the pressure transducer is located proximate to the pressure-inducing device.

11. The non-transitory computer-readable medium of claim 7, wherein the non-transitory computer-readable medium includes program code that is executable by the processing device for causing the processing device to:
classify the pooling or deposition at the pooling or deposition location as a liquid or a solid.

12. The non-transitory computer-readable medium of claim 7, wherein the pressure-inducing device comprises a valve, a fluid-injector, or a pump.

13. The non-transitory computer-readable medium of claim 7, wherein the localized variation in the diameter of the pipe is measured as a distance between a surface of the pooling or deposition and a surface of an opposite end of the pipe.

14. A computer-implemented method comprising:
receiving pressure fluctuations detected by a pressure transducer in a pipe for carrying hydrocarbon fluid in response to a pressure-inducing device of the pipe outputting a pressure signal;
estimating a localized variation in a diameter of the pipe caused by pooling or deposition using an inverse model;
identifying and classifying the pooling or deposition by applying a machine-learning model to the pressure fluctuations;
converting the localized variation in the diameter of the pipe to equivalent liquid volume for pooling locations; and outputting (i) a pooling or deposition location and (ii) outputting a volume that are usable for determining an action on the pipe to remove the pooling or deposition.

15. The computer-implemented method of claim 14, further comprising:
transmitting a command to the pressure-inducing device to cause the pressure-inducing device to generate the pressure signal, wherein the pressure fluctuations detected by the pressure transducer are signal reflections of the pressure signal.

16. The computer-implemented method of claim 14, wherein estimating the localized variation in the diameter of the pipe caused by the pooling or deposition using the inverse model further comprises:
generating an estimated value of the localized variation in the diameter of the pipe;
generating a simulated pressure profile using a forward model based on the pressure signal and estimated value of the localized variation in the diameter of the pipe;
determining an error value between the simulated pressure profile and the pressure fluctuations; and
updating the forward model with an updated estimated value of the localized variation in the diameter of the pipe and repeating the steps of generating the estimated value, generating the simulated pressure profile, and determining the error value until the error value is below a threshold value.

17. The computer-implemented method of claim 14, wherein the pressure transducer is located proximate to the pressure-inducing device.

18. The computer-implemented method of claim 14, wherein the localized variation in the diameter of the pipe is measureable as a distance between a surface of the pooling or deposition and a surface of an opposite end of the pipe.

19. The computer-implemented method of claim 14, wherein classifying the pooling or deposition includes classifying the pooling or deposition as a liquid or a solid.

20. The computer-implemented method of claim 14, wherein the pressure-inducing device comprises a valve, a fluid-injector, or a pump.

* * * * *